(12) United States Patent
Patangay et al.

(10) Patent No.: US 8,951,203 B2
(45) Date of Patent: Feb. 10, 2015

(54) MEASURES OF CARDIAC CONTRACTILITY VARIABILITY DURING ISCHEMIA

(75) Inventors: Abhilash Patangay, Inver Grove Heights, MN (US); Yi Zhang, Plymouth, MN (US); Aaron Lewicke, Forest Lake, MN (US); Julie A. Thompson, Circle Pines, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 838 days.

(21) Appl. No.: 12/761,018

(22) Filed: Apr. 15, 2010

(65) Prior Publication Data

US 2010/0274141 A1 Oct. 28, 2010

Related U.S. Application Data

(60) Provisional application No. 61/171,636, filed on Apr. 22, 2009, provisional application No. 61/257,904, filed on Nov. 4, 2009, provisional application No. 61/257,910, filed on Nov. 4, 2009.

(51) Int. Cl.
- *A61B 5/02* (2006.01)
- *A61N 1/00* (2006.01)
- *A61B 5/0452* (2006.01)
- *A61B 5/024* (2006.01)

(Continued)

(52) U.S. Cl.
CPC .............. *A61B 5/0452* (2013.01); *A61B 5/024* (2013.01); *A61B 5/02405* (2013.01); *G06F 19/3418* (2013.01); *A61B 5/021* (2013.01); *A61B 7/04* (2013.01); *A61B 2562/0219* (2013.01); *A61N 1/3627* (2013.01); *G06F 19/3431* (2013.01)

USPC .............. 600/483; 600/485; 600/528; 607/6; 607/17

(58) Field of Classification Search
CPC .. A61B 5/024; A61B 5/02405; A61B 5/0452; A61B 5/021; A61B 5/02; G06F 19/3418
USPC ................................. 600/300–301, 481–528
See application file for complete search history.

(56) References Cited

U.S. PATENT DOCUMENTS

| 4,936,304 A | 6/1990 | Kresh et al. |
| 5,678,561 A | 10/1997 | Karagueuzian et al. |

(Continued)

FOREIGN PATENT DOCUMENTS

| JP | 2001505441 A | 4/2001 |
| JP | 2005521532 A | 7/2005 |

(Continued)

OTHER PUBLICATIONS

Akay, "Dynamics of Diastolic Sounds Caused by Partially Occluded Coronary Arteries," Feb. 2009, IEEE Transaction on Biomedical Engineering, vol. 56, No. 2, pp. 513-517.*

(Continued)

*Primary Examiner* — Navin Natnithithadha
*Assistant Examiner* — Eric Messersmith
(74) *Attorney, Agent, or Firm* — Schwegman Lundberg & Woessner, P.A.

(57) ABSTRACT

Systems and methods include obtaining a measure of cardiac contractility. A cardiac contractility variability is determined from the measure of cardiac contractility. Analyzing the cardiac contractility variability, an indication of cardio-vasculature health is provided.

18 Claims, 10 Drawing Sheets

(51) Int. Cl.
| | |
|---|---|
| G06F 19/00 | (2011.01) |
| A61B 5/021 | (2006.01) |
| A61B 7/04 | (2006.01) |
| A61N 1/362 | (2006.01) |

(56) References Cited

U.S. PATENT DOCUMENTS

| | | | |
|---|---|---|---|
| 5,682,901 A | 11/1997 | Kamen | |
| 6,021,350 A | 2/2000 | Mathson | |
| 6,077,236 A | 6/2000 | Cunningham | |
| 6,440,078 B1 | 8/2002 | Curiel et al. | |
| 6,775,571 B1 | 8/2004 | Kroll | |
| 7,330,750 B2 | 2/2008 | Erkkila et al. | |
| 7,460,900 B1 | 12/2008 | Gill et al. | |
| 2003/0092998 A1 | 5/2003 | Curiel | |
| 2004/0111033 A1* | 6/2004 | Oung et al. | 600/483 |
| 2004/0215090 A1 | 10/2004 | Erkkila et al. | |
| 2005/0137482 A1 | 6/2005 | Laitio et al. | |
| 2006/0282000 A1* | 12/2006 | Zhang et al. | 600/528 |
| 2007/0032733 A1 | 2/2007 | Burton | |
| 2007/0043299 A1 | 2/2007 | Wariar et al. | |
| 2007/0060962 A1 | 3/2007 | Pappone | |
| 2007/0150015 A1* | 6/2007 | Zhang et al. | 607/17 |
| 2007/0244402 A1 | 10/2007 | Brockway et al. | |
| 2008/0154144 A1 | 6/2008 | Unver et al. | |
| 2010/0113954 A1 | 5/2010 | Zhou | |
| 2010/0274147 A1 | 10/2010 | Patangay et al. | |

FOREIGN PATENT DOCUMENTS

| | | |
|---|---|---|
| JP | 2012524614 A | 10/2012 |
| JP | 2012524615 A | 10/2012 |
| WO | WO-2010/123749 A2 | 10/2010 |
| WO | WO-2010/123751 A1 | 10/2010 |

OTHER PUBLICATIONS

"International Application Serial No. PCT/US2010/031220, International Search Report mailed Dec. 7, 2010", 8 pgs.

"International Application Serial No. PCT/US2010/031220, Invitation to Pay Additional Fees and Partial International Search Report mailed Jul. 14, 2010", 10 pgs.

"International Application Serial No. PCT/US2010/031220, Written Opinion mailed Dec. 7, 2010", 13 pgs.

"International Application Serial No. PCT/US2010/031227, International Search Report mailed Jun. 29, 2010", 6 pgs.

"International Application Serial No. PCT/US2010/031227, Written Opinion mailed Jun. 29, 2010", 9 pgs.

Ahlstrom, C, et al., "Assessing Aortic Stenosis Using Sample Entropy of the Phonocardiographic Signal in Dogs", *IEEE Transactions on Biomedical Engineering*, 55(8), (2008), 2107-2109.

Akay, M, et al., "Dynamics of Diastolic Sounds Caused by Partially Occluded Coronary Arteries", *IEEE Transactions on Biomedical Engineering*, 56(2), (2009), 513-517.

Amit, G. et al., "Acoustic Indices of Cardiac Functionality", *International Conference on Bio-Inspired Systems and Signal Processing (BIOSIGNALS)*, vol. 2, [online]. [retrieved Jun. 17, 2010]. Retrieved from the Internet: <URL:http://www.cs.tau.ac.il/{gamit/papers/Amit_BIOSTEC_08.pdf>, (2008), 77-83.

Gomis, P., et al., "Non-Linear dynamic analysis of the cardiac rhythm during transient myocardial ischemia", *Biomedizinische Technik*, 51(4), (2006), 178-181.

Kannathal, N., et al., "Cardiac state diagnosis using adaptive neuro-fuzzy technique", *Medical Engineering & Physics*, 28(8), (2006), 809-815.

Nigam. V., et al., "Accessing heart dynamics to estimate durations of heart sounds", *Physiolocical Measurement*, 26(6), (2005). 1005-1018.

Patangay, A., et al., "Measures of Cardiac Contractility Variability during Ischemia", *31st Annual International Conference of the EEE EMBS*, (Minneapolis, Minnesota, Sep. 2-6, 2009), 4198-4201.

Peng, Y., et al., "Heart Rate Variability in Myocardial Ischemic Periods", *IEEE Engineering in Medicine and Biology Magazine*, 27(5), (2008), 14-19.

Voss, A., et al., "Methods derived from nonlinear dynamics for analysing heart rate variability", *Philosophical Transactions of the Royal Society A*, 367, (1887), (2009), 277-296.

Wennerblom, B., et al., "Reduced heart rate variability in ischemic heart disease is only partially caused by ischemia. An HRV study before and after PTCA", *Cardiology*, 94(3), (2000), 146-151.

Kamen, P. W, et al., "Poincaré plot of heart rate variability allows quantitative display of parasympathetic nervous activity in humans.", *Clin Sci (Lond)*, 91(2), (Aug. 1996), 201-8.

Khandoker, A. H., et al., "Identifying diabetic patients with cardiac autonomic neuropathy by heart rate complexity analysis", *BioMedical Engineering OnLine*, 8(3), (2009), 12 pgs.

Lewicke, A., et al., "Heart Rate Variability Among Infants Who Have Cardio-Respiratory Events", *Pediatric Academic Society*, Abstract, (Sep. 2006).

Lewicke, A., et al., "Heart rate variability for predicting cardiorespiratory events in infants", *Journal of Electrocardiology*, 39(4), Supplement, (Oct. 2006), S83.

Xiao, Shouzhong, et al., "Studying Cardiac Contractility Change Trend to Evaluate Cardiac Reserve", *IEEE Engineering in Medicine and Biology*, (Jan./Feb. 2002), 74-76.

Xiao, Shouzhong, et al., "Studying the significance of cardiac contractility variability", *IEEE Engineering in Medicine and Biology Magazine*, 19(3), (May-Jun. 2000), 102-105.

"U.S. Appl. No. 12/761,047, Response filed Aug. 17, 2012 to Final Office Action mailed Apr. 30, 2012", 15 pgs.

"U.S. Appl. No. 12/761,047, Response filed Jan. 10, 2012 to Final Office Action mailed Apr. 30, 2012", 14 pgs.

"U.S. Appl. No. 12/761,047, Advisory Action mailed Aug. 30, 2012", 3 pgs.

"U.S. Appl. No. 12/761,047, Examiner Interview Summary mailed Sep. 28, 2012", 4 pgs.

"U.S. Appl. No. 12/761,047, Final Office Action mailed Apr. 30, 2012", 17 pgs.

"U.S. Appl. No. 12/761,047, Non Final Office Action mailed Nov. 8, 2011", 14 pgs.

"U.S. Appl. No. 12/761,047, Response filed Feb. 29, 2012 to Non Final Office Action mailed Nov. 8, 2011", 12 pgs.

"European Application Serial No. 10714799.3, Response filed Jul. 17, 2012 to Office Action mailed Jan. 13, 2012", 18 pgs.

"International Application Serial No. PCT/US2010/031220, International Preliminary Report on Patentability mailed Nov. 3, 2011", 13 pgs.

"International Application Serial No. PCT/US2010/031227, International Preliminary Report on Patentability mailed Nov. 3, 2011", 9 pgs.

"Japanese Application Serial No. 2012-507268, Voluntary Amendments filed on Apr. 18, 2012", With English Translation, 6 pgs.

"U.S. Appl. No. 12/761,047, Non Final Office Action mailed Apr. 24, 2014", 16 pgs.

"Japanese Application Serial No. 2012-507268, Office Action mailed Jul. 8, 2014", With English Translation, 10 pgs.

"Japanese Application Serial No. 2012-507268, Office Action mailed Aug. 6, 2013", With English Translation, 14 pgs.

"Japanese Application Serial No. 2012-507268, Response filed Nov. 14, 2013 to Office Action mailed Aug. 6, 2013", With English Claims, 11 pgs.

"Japanese Application Serial No. 2012-507270, Office Action mailed Aug. 6, 2013", With English Translation, 6 pgs.

* cited by examiner

| Metric (units when measured for RR interval) | Correlation Coefficient for change in HRV metric with change in max dP/dT | Correlation Coefficient for change in S1 metric with change in max dP/dT |
|---|---|---|
| Mean [msec] | -0.7066 | -0.4705 |
| Median [msec] | -0.6988 | -0.512 |
| SDNN [msec] | -0.8852† | 0.0399 |
| IQRNN [msec] | -0.973† | 0.0608 |
| CV [NA] | -0.8878† | -0.5298 |
| SDSD [msec] | -0.4397 | 0.4271 |
| IQRSD [msec] | -0.6182 | 0.6623 |
| NIQRSD [msec] | -0.5876 | -0.4077 |
| RMSSD [msec] | -0.4931 | 0.5287 |
| CVS [NA] | -0.4891 | -0.4688 |
| pNN50 [%] | -0.5736 | -0.4563 |
| HF [msec$^2$] | -0.5662 | -0.5557 |
| LF [msec$^2$] | -0.5806 | -0.5552 |
| Total Power [msec$^2$] | -0.5929 | -0.5554 |
| LF/HF [NA] | -0.4628 | -0.511 |
| HFW [msec$^2$] | -0.6029 | -0.5789 |
| LFW [msec$^2$] | -0.6962 | -0.4653 |
| LFW/HFW [NA] | -0.4795 | -0.723 |
| ApEn [regularity] | 0.6802 | 0.9605† |
| SigXY [scatter] | -0.9224† | 0.0852 |
| FD [space filling] | -0.5554 | 0.1747 |
| DFA1 [slope] | -0.8055 | -0.457 |
| DFA2 [slope] | -0.8412† | -0.8057† |

MEASURES OF CARDIAC CONTRACTILITY VARIABILITY DURING ISCHEMIA

CROSS-REFERENCE TO RELATED APPLICATIONS

This application claims the benefit of U.S. Provisional Application Nos. 61/171,636, filed on Apr. 22, 2009; 61/257,904, filed on Nov. 4, 2009; and 61/257,910, filed on Nov. 4, 2009, under 35 U.S.C. §119(e), which are hereby incorporated by reference in their entirety.

BACKGROUND

The heart is the center of a person's circulatory system. It includes an electro-mechanical system performing two major pumping functions. The left portions of the heart draw oxygenated blood from the lungs and pump it to the organs of the body to provide oxygen. The right portions of the heart draw deoxygenated blood from the organs and pump it to the lungs where the blood is oxygenated. These pumping functions result from contractions of the myocardium, or heart muscle. In a normal heart, the sinoatrial node, the heart's natural pacemaker, generates electrical impulses that propagate through an electrical conduction system to various regions of the heart and excite the myocardial tissues of these regions. In a normal electrical conduction system, coordinated delays in the propagations of the electrical impulses cause the various portions of the heart to contract in synchrony to provide efficient pumping functions. A blocked or otherwise abnormal electrical conduction and/or deteriorated myocardial tissue can cause dysynchronous contraction of the heart. The dysynchrony can be characterized as an arrhythmia, which can further be characterized as bradycardias, tachycardias, automaticity, re-entry arrhythmias, and fibrillation, among others. The existence of an arrhythmia can result in poor hemodynamic performance and diminished blood supply.

Ischemia is a condition where a portion of a body is deprived of adequate oxygen and metabolite removal due to an interruption in blood supply caused by an occlusion of a blood vessel. One example of ischemia is cardiac ischemia. It follows then that cardiac ischemia is a condition in which the myocardium is deprived of adequate oxygen and metabolite removal due to an interruption in blood supply, such as resulting from an occlusion of a coronary artery.

Myocardial infarction (MI) is the necrosis of portions of the myocardial tissue resulted from cardiac ischemia. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

OVERVIEW

The present inventors have recognized, among other things, that early detection and diagnosis of patient conditions that precede or coincide with arrhythmias, cardiac ischemia, myocardial infarction, and other cardiac indications is important.

Example 1 describes a system comprising a machine-readable media. The machine-readable media can include instructions, which when executed by the one or more processors, cause the one or more processors to obtain a measure of cardiac contractility. From the measure of cardiac contractility, a cardiac contractility variability can be determined. Then the cardiac contractility variability can be analyzed to provide an indication of cardio-vasculature health.

In Example 2, the system of Example 1 can be optionally configured to obtain a measure of at least one of a heart sound, a pulmonary artery pressure, a coronary venous pressure, a left ventricular pressure, a right ventricular pressure, or a timing interval to provide the measure of cardiac contractility.

In Example 3, the systems of Example 1 or 2 can be optionally configured such that the instructions to determine the cardiac contractility variability comprise instructions to use a time domain variability parameter to measure cardiac contractility variability.

In Example 4, the systems of any one or more of Examples 1-3 can be optionally configured such that the instructions to determine the cardiac contractility variability comprise instructions to use a frequency domain variability parameter to measure cardiac contractility variability.

In Example 5, the systems of any one or more of Examples 1-4 can be optionally configured such that the instructions to determine the cardiac contractility variability comprise instructions to use a time-frequency domain variability parameter to measure cardiac contractility variability.

In Example 6, the systems of any one or more of Examples 1-5 can be optionally configured such that the instructions to determine the cardiac contractility variability comprise instructions to use a nonlinear variability parameter to measure cardiac contractility variability.

In Example 7, the systems of any one or more of Examples 1-6 can be optionally configured such that the instructions to use the parameter from the class of nonlinear variability parameters comprise instructions to measure an approximate entropy (ApEn) of an S1 amplitude.

In Example 8, the systems of any one or more of Examples 1-7 can be optionally configured such that the instructions to determine the cardiac contractility variability is performed using a time period to provide a variability measurement and the instructions to analyze the cardiac contractility variability comprise instructions to trend the variability measurement to provide a trended variability measurement. The one or more processors can then compare the trended variability measurement to a threshold value to provide a comparison. Using the comparison, the one or more processors detect a cardiac state.

In Example 9, the systems of any one or more of Examples 1-8 can be optionally configured such that the time period is an epoch having a duration of thirty seconds to twenty-four hours.

In Example 10, the systems of any one or more of Examples 1-9 can be optionally configured comprising instructions, which when executed by the one or more processors, cause the one or more processors to after determining the cardiac contractility variability, adjust at least one of: a CRT timing parameter or an electrical position. The one or more processors can then measure the contractility variability after the adjusting and continue to adjust in a closed-loop feedback manner to increase the cardiac contractility variability.

In Example 11, the systems of any one or more of Examples 1-10 can be optionally configured comprising instructions, which when executed by the one or more processors, cause the one or more processors to normalize the cardiac contractility variability by the measure of cardiac contractility.

In Example 12, the systems of any one or more of Examples 1-11 can be optionally configured comprising instructions, which when executed by the one or more processors, cause the one or more processors to normalize the cardiac contractility variability by an associated heart rate.

Example 13 describes a method comprising obtaining a measure of cardiac contractility; determining a cardiac contractility variability from the measure of cardiac contractility; and analyzing the cardiac contractility variability to provide an indication of cardio-vasculature health.

In Example 14, the method of Example 13 can be optionally performed such that obtaining the measure of cardiac contractility comprises obtaining a measure of at least one of a heart sound, a pulmonary artery pressure, a coronary venous pressure, a left ventricular pressure, a right ventricular pressure, or a timing interval to provide the measure of cardiac contractility.

In Example 15, the methods of Examples 13 or 14 can be optionally performed such that determining the cardiac contractility variability comprises using a time domain variability parameter to measure cardiac contractility variability.

In Example 16, the methods of any one or more of Examples 13-15 can be optionally performed such that determining the cardiac contractility variability comprises using a frequency domain variability parameter to measure cardiac contractility variability.

In Example 17, the methods of any one or more of Examples 13-16 can be optionally performed such that determining the cardiac contractility variability comprises using a time-frequency domain variability parameter to measure cardiac contractility variability.

In Example 18, the methods of any one or more of Examples 13-17 can be optionally performed such that determining the cardiac contractility variability comprises using a nonlinear variability parameter to measure cardiac contractility variability.

In Example 19, the methods of any one or more of Examples 13-18 can be optionally performed such that using the parameter from the class of nonlinear variability parameters comprises measuring an approximate entropy (ApEn) of an S1 amplitude.

In Example 20, the methods of any one or more of Examples 13-19 can be optionally performed such that determining the cardiac contractility variability is performed using a time period to provide a variability measurement and analyzing the cardiac contractility variability comprises trending the variability measurement to provide a trended variability measurement; comparing the trended variability measurement to a threshold value to provide a comparison; and using the comparison to detect a cardiac state.

In Example 21, the methods of any one or more of Examples 13-20 can be optionally performed such that the time period is an epoch having a duration of thirty seconds to twenty-four hours.

In Example 22, the methods of any one or more of Examples 13-21 can be optionally performed further comprising after determining the cardiac contractility variability, adjusting at least one of: a CRT timing parameter, a lead position, or an electrical position; measuring the contractility variability after the adjusting; and continuing adjusting in a closed-loop feedback manner to increase the cardiac contractility variability.

In Example 23, the methods of any one or more of Examples 13-22 can be optionally performed further comprising normalizing the cardiac contractility variability by the measure of cardiac contractility.

In Example 24, the methods of any one or more of Examples 13-23 can be optionally performed further comprising normalizing the cardiac contractility variability by an associated heart rate.

Example 25 describe an apparatus comprising a memory device and a sensor device coupled to the memory device, the sensor configured to sense a plurality of indications of a plurality of cardiac cycles, and to store the plurality of indications of the plurality of cardiac cycles in the memory device. The apparatus includes means for obtaining a measure of cardiac contractility using the plurality of indications of the plurality of cardiac cycles. The apparatus also includes means for determining a cardiac contractility variability from the measure of cardiac contractility and means for analyzing the cardiac contractility variability to provide an indication of cardio-vasculature health.

This overview is intended to provide an overview of subject matter of the present patent application. It is not intended to provide an exclusive or exhaustive explanation. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 6 is a table illustrating relationships between RR interval-based variability metrics, contractility variability metrics, and max dP/dT;

DETAILED DESCRIPTION

The examples described herein include systems and methods for measuring and using the measures of cardiac contractility variability. Cardiac contractility is generally understood as the degree to which muscle fibres can shorten when activated by a stimulus independent of preload and afterload. Contractility can be used as a measure of myocardial performance. A measure of myocardial contractility can be obtained in different ways, such as by using an ejection fraction, a rate of pressure change during ventricular contraction, coronary venous or artery pressures, or surrogates of such measurements.

In a chronic heart failure (CHF) patient, contractility can change over time. While recording and trending contractility over time can provide some prognostic and diagnostic value, the variability of contractility can be used to provide additional insight into a patient's ongoing condition. Hence, in a way analogous to heart rate and heart rate variability, the variability of contractility during a particular period of time can provide different information than just comparing the contractility at the beginning and end of the same period. Similarly, trending the variability of contractility can provide different information than trending contractility at discrete points in time. The following discusses various systems and methods to calculate and use cardiac contractility variability (CCV) measures.

System Overview

Figure 1:
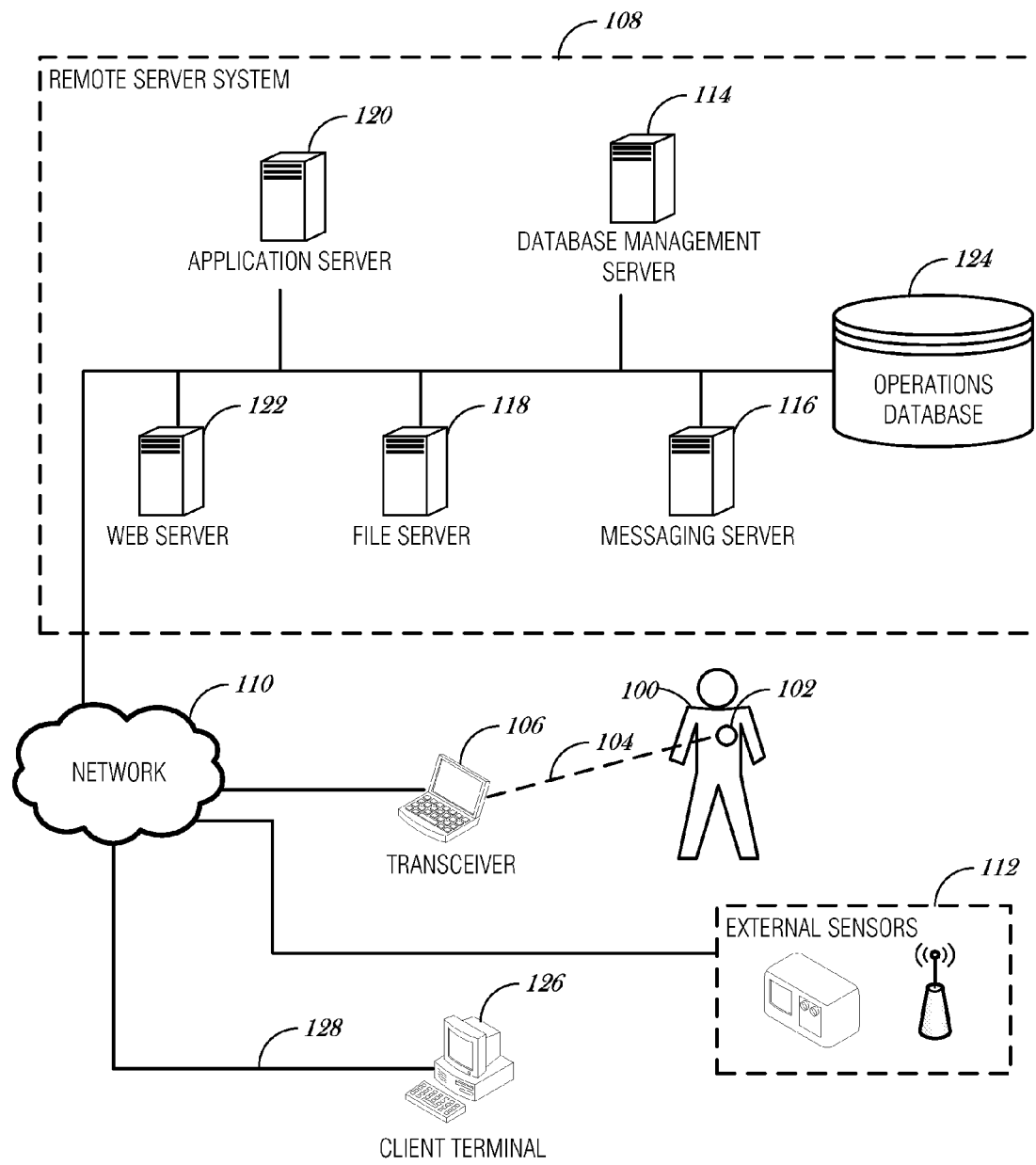
FIG. 1 illustrates portions of a system that enables physician-patient communication.

FIG. 1 illustrates portions of a system that enables physician-patient communication. In the example of FIG. 1, a patient 100 can be provided with an ambulatory or implantable medical device (IMD) 102. Examples of implantable medical devices include a pacemaker, an implantable cardioverter defibrillator (ICD), a cardiac resynchronization therapy pacemaker (CRT-P), a cardiac resynchronization therapy defibrillator (CRT-D), a pulmonary artery (PA) pressure sensor, a neurostimulation device, a deep brain stimulation device, a cochlear implant or a retinal implant. In some examples, the IMD 102 can be capable of sensing physiological data, deriving physiological measures/correlations, and storing data for later communication or reference. Examples of physiological data include implantable electrograms, surface electrocardiograms, heart rate intervals (e.g., AA, VV, AV or VA intervals), electrogram templates such as for tachyarrhythmia discrimination, pressure (e.g., intracardiac or systemic pressure), oxygen saturation, activity, heart rate variability, heart sounds, impedance, respiration, intrinsic depolarization amplitude, or the like. While only one IMD 102 is illustrated in FIG. 1, it is understood that more than one IMD 102 may be implanted. For example, medical devices that have specific functions can be placed in accordance with their function. In addition, the IMD 102 can be composed of more than one device, with each device having one or more functions.

The IMD 102 can be capable of bidirectional communication using a connection 104 with a computing device 106. A computing device can be a device capable of receiving input, processing instructions, storing data, presenting data in a human-readable form, and communicating with other devices. In some cases, a computing device can be referred to as a "transceiver." The IMD 102 receives commands from the computing device 106 and can also communicate one or more patient indications to the computing device 106. Examples of patient indications include sensed or derived measurements such as heart rate, heart rate variability, data related to tachyarrhythmia episodes, hemodynamic stability, activity, therapy history, autonomic balance motor trends, electrogram templates for tachy discrimination, heart rate variability trends or templates, or trends, templates, or abstractions derived from sensed physiological data. Patient indications include one or more physiological indications, such as the physiological data described above. The IMD 102 can also communicate one or more device indications to the computing device 106. Examples of device indications include lead/shock impedance, pacing amplitudes, pacing thresholds, or other device metrics. In certain examples, the IMD 102 can communicate sensed physiological signal data to the computing device 106, which can then communicate the signal data to a remote device for processing.

Typically, the computing device 106 can be located in close proximity to the patient 100. The computing device 106 can be attached, coupled, integrated or incorporated with a personal computer or a specialized device, such as a medical device programmer. In an example, the computing device 106 can be a hand-held device. In examples, the computing device 106 can be a specialized device or a personal computer. In an example, the computing device 106 can be adapted to communicate with a remote server system 108. The communication link between the computing device 106 and the remote server system 108 can be made through a computer or telecommunications network 110. The network 110 can include, in various examples, one or more wired or wireless networking such as the Internet, satellite telemetry, cellular telemetry, microwave telemetry, or other long-range communication networks.

In an example, one or more ambulatory or non-ambulatory external sensors 112 can be adapted to communicate with the computing device 106 or the remote server system 108 and can transmit and receive information, such as sensed data. External sensors 112 can be used to measure patient physiological data, such as temperature (e.g., a thermometer), blood pressure (e.g., a sphygmomanometer), blood characteristics (e.g., glucose level), body weight, physical strength, mental acuity, diet, or heart characteristics. An external sensor 112 can also include one or more environmental sensors. The external sensors 112 can be placed in a variety of geographic locations (in close proximity to patient or distributed throughout a population) and can record non-patient specific characteristics such as, for example, temperature, air quality, humidity, carbon monoxide level, oxygen level, barometric pressure, light intensity, and sound.

External sensors 112 can also include devices that measure subjective data from the patient. Subjective data includes information related to a patient's feelings, perceptions, and/or opinions, as opposed to objective physiological data. For example, the "subjective" devices can measure patient responses to inquiries such as "How do you feel?", "How is your pain?" and "Does this taste good?" Such a device can also be adapted to present interrogatory questions related to observational data, such as "What color is the sky?" or "Is it sunny outside?" The device can prompt the patient and record responsive data from the patient using visual and/or audible cues. For example, the patient can press coded response buttons or type an appropriate response on a keypad. Alternatively, responsive data can be collected by allowing the patient to speak into a microphone and using speech recognition software to process the response.

In some examples, the remote server system 108 comprises one or more computers, such as a database server 114, a messaging server 116, a file server 118, an application server 120 and a web server 122. The database server 114 can be configured to provide database services to clients, which can be other servers in the remote server system 108. The messaging server 116 can be configured to provide a communication platform for users of the remote server system 108. For example, the messaging server 116 can provide an email communication platform. Other types of messaging, such as short message service (SMS), instant messaging, or paging services can be used. The file server 118 can be used to store documents, images, and other files for the web server 122 or as a general document repository. The application server 120 can provide one or more applications to the web server 122 or provide client-server applications to the client terminals 126. To enable some of these services provided by these servers 114, 116, 118, 120, and 112, the remote server system 108 can include an operations database 124. The operations database 124 can be used for various functions and can be composed of one or more logically or physically distinct databases. The operations database 124 can be used to store clinician data for individual patients, patient populations, patient trials, and the like. In addition, the operations database 124 can be used to store patient data for individual patients, patient populations, patient trials, and the like. For example, the operations database 124 can include a copy of, a portion of, a summary of, or other data from an electronic medical records system. In addition, the operations database 124 can store device information, such as device settings for a particular patient or a group of patients, preferred device settings for a particular clinician or a group of clinicians, device manufacturer information, and the like. In addition, the operations database 124 can be used to store raw, intermediate, or summary data of patient indications along with probabilistic outcomes (e.g., a patient population profile and a corresponding 1-year survival curve).

In an example, one or more client terminals 126 can be locally or remotely connected to the remote server system 108 via network 110. The client terminals 112 can be communicatively coupled to the remote server system 108 using a connection 128, which can be wired or wireless in various examples. Examples of client terminals 126 can include personal computers, dedicated terminal consoles, handheld devices (e.g., a personal digital assistant (PDA) or cellular telephone), or other specialized devices (e.g., a kiosk). In various examples, one or more users can use a client terminal 126 to access the remote server system 108. For example, a customer service professional can use a client terminal 126 to access records stored in the remote server system 108 to update patient records. As another example, a physician or clinician can use a client terminal 126 to receive or provide patient-related data, such as comments regarding a patient visit, physiological data from a test or collected by a sensor or monitor, therapy history (e.g., IMD shock or pacing therapy), or other physician observations.

In some examples, the IMD 102 can be adapted to store patient data and to use the data to provide tailored therapy. For example, using historical physiological data, an IMD 102 can be able to discriminate between lethal and non-lethal heart rhythms and deliver an appropriate therapy. However, it can be desirable to establish a proper baseline of historical data by collecting a sufficient amount of data in the IMD 102. In some examples, a "learning period" of some time (e.g., thirty days) can be used to establish the baseline for one or more physiological signals. An IMD 102 can, in an example, store a moving window of data of operation, such as a time period equal to the learning period, and can use the information as a baseline indication of the patient's biorhythms or biological events.

Once the baseline is established, then acute and chronic patient conditions can be determined probabilistically. The baseline can be established by using historical patient records or by comparing a patient to a population of patients. In an example, a diagnostic technique uses a patient-based baseline to detect a change in a patient's condition over time. Examples of a diagnostic technique that uses a patient-derived baseline are described in the next section.

In an example, patient diagnostics can be automatically collected and stored by the IMD 102. These values can be based on the patient's heart rate or physical activity over a time period (e.g., 24-hour period) and each diagnostic parameter can be saved as a function of the time period. In one example, heart-rate based diagnostics utilize only normal intrinsic beats. For heart rate variability (HRV) patient diagnostics, the average heart rate can be found at each interval within the time period, for example, at each of the 288 five-minute intervals occurring during 24 hours. From these interval values, the minimum heart rate (MinHR), average heart rate (AvgHR), maximum heart rate (MaxHR) and standard deviation of average normal-to-normal (SDANN) values can be calculated and stored. In one example, the IMD 102 computes a HRV FOOTPRINT® patient diagnostic that can include a 2-dimensional histogram that counts the number of daily heartbeats occurring at each combination of heart rate (interval between consecutive beats) and beat-to-beat variability (absolute difference between consecutive intervals). Each histogram bin contains the daily total for that combination. The percentage of histogram bins containing one or more counts can be saved each day as the footprint percent (Footprint %). The IMD 102 can also provide an ACTIVITY LOG® patient diagnostic (Activity %), which can include a general measure of patient activity and can be reported as the percentage of each time period during which the device-based accelerometer signal is above a threshold value.

In other examples, HRV can be calculated using one or more time, frequency, time-frequency, or nonlinear measurements, either alone or in combination. Twenty-three variability parameters that can be used in this type of calculation include eleven time domain metrics: mean, median, standard deviation of normal-to-normal beats (SDNN), inter-quartile range of normal-to-normal beats (IQRNN), coefficient of variation (CV), standard deviation of successive differences (SDSD), inter-quartile range of successive differences (IQRSD), normalized IQRSD (NIQRSD), root-mean-square of successive differences (RMSSD), coefficient of variation for successive differences (CVS) and percentage of differences between adjacent normal-to-normal intervals that are >50 msec (pNN50); four frequency domain metrics: power in the high- and low-frequency range (HF, LF), power ratio (LF/HF), and total power; three time-frequency metrics: high- and low-frequency wavelet power (HFW, LFW) and power ratio (LFW/HFW); and five nonlinear metrics: approximate entropy (ApEn), X-Y scatter from Poincaré plot (SigXY), fractal dimension (FD), and detrended fluctuation analysis (DFA1 and DFA2). Variability parameters associated with the five nonlinear metrics, in addition to other metrics that are not one of the time, frequency, or time-frequency type of metrics, can be referred to generally as "class of nonlinear metrics." Thus, when referring to a class of nonlinear metrics, for the purposes of this discussion, such reference will be understood to be including the five known nonlinear metrics and any other heart rate variability metrics that are later recognized as being nonlinear metrics (i.e., metrics that are not classified as being time, frequency, or time-frequency metrics).

Figure 2:
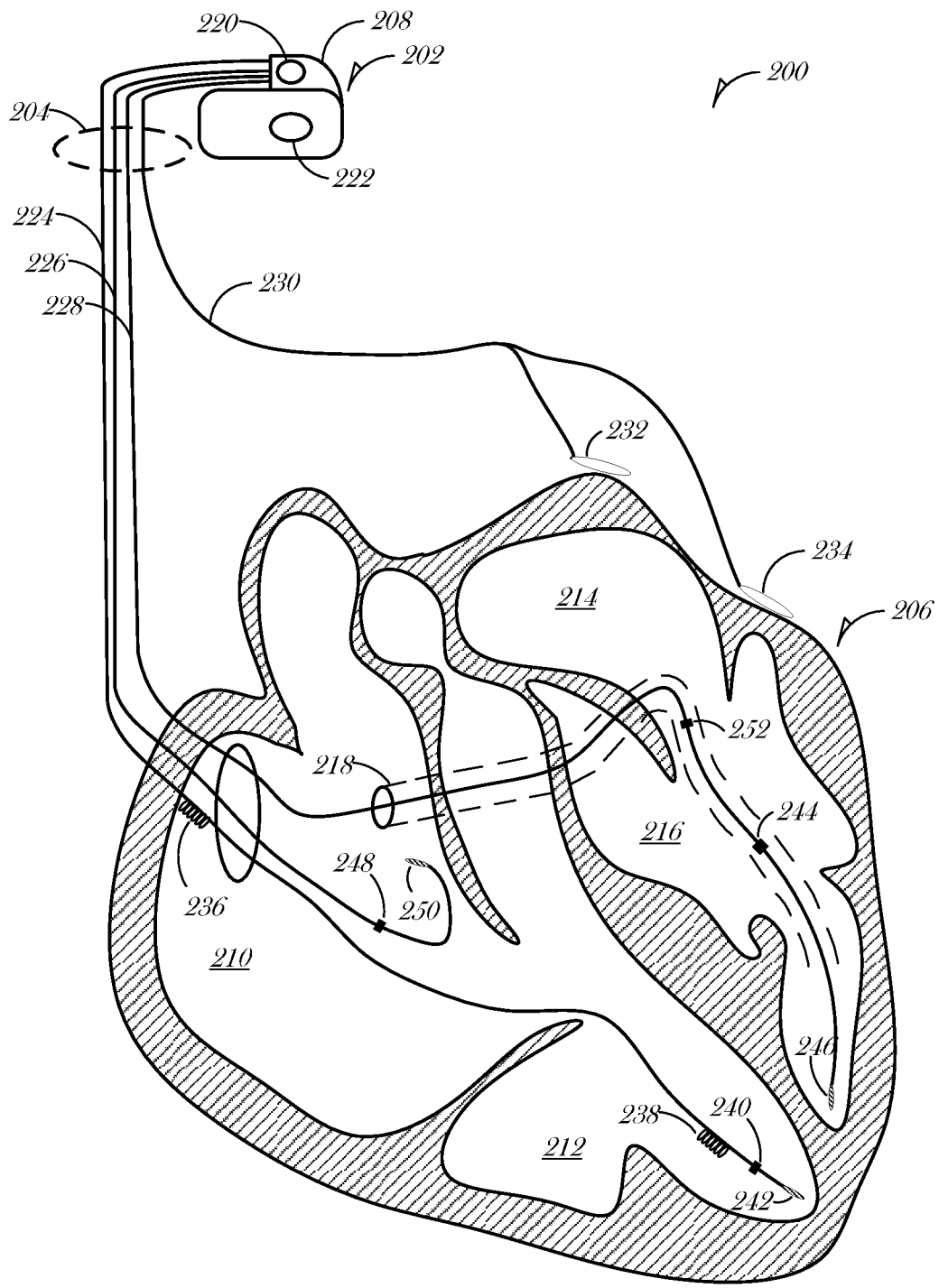
FIG. 2 is a schematic diagram illustrating an implanted medical device (IMD) system.

FIG. 2 is a schematic diagram illustrating an implanted medical device (IMD) system 200. The IMD system 200 includes an IMD 202 coupled to a lead system 204 deployed within a heart 206. The lead system 206 can be designed for implantation in a coronary vein for purposes of cardiac resynchronization therapy (CRT). The lead system 206 can be coupled to the IMD 202, which includes a detection/energy delivery system 208 that actively measures and controls the lead system 206 to provide cardiac pacing therapy.

The detector/energy delivery system 208 typically includes a power supply and programmable circuit (e.g., microprocessor) coupled to an analog to digital (A-D) converter (not shown). Various lead system devices, such as electrodes and pressure sensors, can interface to the A-D converter for sensing/data collection. Alternatively, analog conditioning (e.g., filtering) can be applied to sensor signals before interfacing with the A-D converter. The detector/energy delivery system 208 also utilizes an energy delivery system (not shown). The energy delivery system can include charge capacitors and signal conditioning circuitry. The energy system can interface to the programmable circuit through a D-A converter. Components and functionality of the detector/energy delivery system 208 will be further described below with reference to FIG. 3.

The IMD system 200 can be used to implement methods for therapy control based on electromechanical timing. The IMD 202 can be electrically and physically coupled to the lead system 204. The housing and/or header of the IMD 202 can incorporate one or more electrodes 220 and 222 used to provide electrical stimulation energy to the heart 206 and to sense cardiac electrical activity. The IMD 202 can utilize all or a portion of the IMD housing as a can electrode 222. The IMD 202 can include an indifferent electrode 220 positioned, for example, on the header or the housing of the IMD 202. If the IMD 202 includes both a can electrode 222 and an indifferent electrode 220, the electrodes 220 and 222 can be electrically isolated from each other.

The heart 206 includes several physiological structures, including a right atrial chamber 210, a right ventricle 212, left atrial chamber 214, and left ventricle 216. The lead system 204 can be implanted into the coronary sinus using various techniques. One such technique, as illustrated in FIG. 2, involves creating an opening in a percutaneous access vessel such as the left subclavian or left cephalic vein. The pacing lead can be guided into the right atrial chamber 210 of the heart via the superior vena cava. From the right atrial chamber 210, the lead system 204 can be sent into the coronary sinus ostium. The ostium is the opening of a coronary sinus 218 into the right atrial chamber 210. The lead system 204 can be guided through the coronary sinus 218 to a coronary vein of the left ventricle 216. A distal end of the lead system 204 can be lodged into the coronary vein.

The lead system 204 can be used to provide pacing signals to the heart 206, detect electric cardiac signals produced by the heart 206, sense blood oxygen saturation, and can also be used to provide electrical energy to the heart 206 under certain predetermined conditions to treat cardiac conditions, such as arrhythmias. The lead system 204 can include one or more electrodes used for pacing, sensing, and/or defibrillation. In the example shown in FIG. 2, the lead system 204 includes an intracardiac right ventricular (RV) lead system 224, an intracardiac right atrial (RA) lead system 226, an intracardiac left ventricular (LV) lead system 228, and an extracardiac left atrial (LA) lead system 230. The lead system 204 can be used for therapy based on electromechanical timing methodologies. Other leads and/or electrodes can additionally or alternatively be used.

The lead system 204 can include intracardiac leads 224, 226, 228 implanted in a human body with portions of the intracardiac leads 224, 226, 228 inserted into the heart 206. The intracardiac leads 224, 226, 228 include one or more electrodes positionable within the heart 206 for sensing electrical activity of the heart 206 and for delivering electrical stimulation energy to the heart 206, for example, pacing pulses and/or defibrillation shocks to treat various arrhythmias.

The lead system 204 can also include one or more extracardiac leads 230 having electrodes, e.g., epicardial electrodes or sensors 232 and 234, positioned at locations outside the heart 206 for sensing and/or pacing one or more heart chambers.

The right ventricular lead system 224 includes an SVC-coil 236, an RV-coil 238, an RV-tip electrode 240, and an RV-ring electrode 242. The right ventricular lead system 224 extends through the right atrium 210 and into the right ventricle 212. In particular, the RV-tip electrode 240, RV-ring electrode 242, and RV-coil electrode 238 can be positioned at appropriate locations within the right ventricle 212 for sensing and delivering electrical stimulation pulses to the heart. The SVC-coil 236 can be positioned at an appropriate location within the right atrium chamber 210 of the heart 206 or a major vein leading to the right atrial chamber 210.

In one configuration, the RV-tip electrode 240 referenced to the can electrode 222 can be used to implement unipolar pacing and/or sensing in the right ventricle 212. Bipolar pacing and/or sensing in the right ventricle 212 can be implemented using the RV-tip 240 and RV-ring 242 electrodes. In yet another configuration, the RV-ring 242 electrode can optionally be omitted and bipolar pacing and/or sensing can be accomplished using the RV-tip electrode 240 and the RV-coil 238, for example. The right ventricular lead system 224 can be configured as an integrated bipolar pace/shock lead. The RV-coil 238 and the SVC-coil 236 can be defibrillation electrodes.

The left ventricular lead 228 includes an LV distal electrode 244 and an LV proximal electrode 246 located at appropriate locations in or about the left ventricle 216 for pacing and/or sensing the left ventricle 216. The left ventricular lead 228 can be guided into the right atrium 210 of the heart via the superior vena cava. From the right atrium 210, the left ventricular lead 228 can be deployed into the coronary sinus ostium, the opening of the coronary sinus 218. The left ventricle lead 228 can be guided through the coronary sinus 218 to a coronary vein of the left ventricle 216. This vein can be used as an access pathway for leads to reach the surfaces of the left ventricle 216 which are not directly accessible from the right side of the heart, and to sense blood oxygen levels in the blood leaving the myocardium. Lead placement for the left ventricular lead 228 can be achieved via subclavian vein access and a preformed guiding catheter for insertion of the LV electrodes 244 and 246 proximate to the left ventricle.

Unipolar pacing and/or sensing in the left ventricle 216 can be implemented, for example, by using the LV distal electrode 244 referenced to the can electrode 222. The LV distal electrode 244 and the LV proximal electrode 246 can be used together as bipolar sense and/or pace electrodes for the left ventricle 216. The left ventricular lead 228 and the right ventricular lead 224, in conjunction with the IMD 202, can be used to provide cardiac resynchronization therapy such that the ventricles of the heart can be paced substantially simultaneously, or in phased sequence, to provide enhanced cardiac pumping efficiency for patients suffering from various symptoms of heart failure.

The right atrial lead 226 includes a RA-tip electrode 248 and an RA-ring electrode 250 positioned at appropriate locations in the right atrium 210 for sensing and pacing the right atrium 210. In one configuration, the RA-tip electrode 248 referenced to the can electrode 222, for example, can be used to provide unipolar pacing and/or sensing in the right atrium 210. In another configuration, the RA-tip electrode 248 and the RA-ring electrode 250 can be used to provide bipolar pacing and/or sensing.

The left ventricular lead 228 can include a pressure transducer 252. The pressure transducer 252 can be a micro-electrical-mechanical system (MEMS), for example. MEMS technology uses semiconductor techniques to build microscopic mechanical devices in silicon or similar materials. The pressure transducer 252 can include a micromachined capacitive or piezoresistive transducer exposed to the bloodstream. Other pressure transducer technologies, such as resistive strain gages can also be employed as a pressure transducer 252. The pressure transducer 252 can be coupled to one or more conductors disposed along the length of the left ventricular lead 228. The pressure transducer 252 can be integrated with the left ventricular lead 228. Transducers such as the pressure transducer 252 can be used to determine pulmonary arterial (PA) pressure information useful for determining electromechanical delay (EMD) information.

Figure 3:
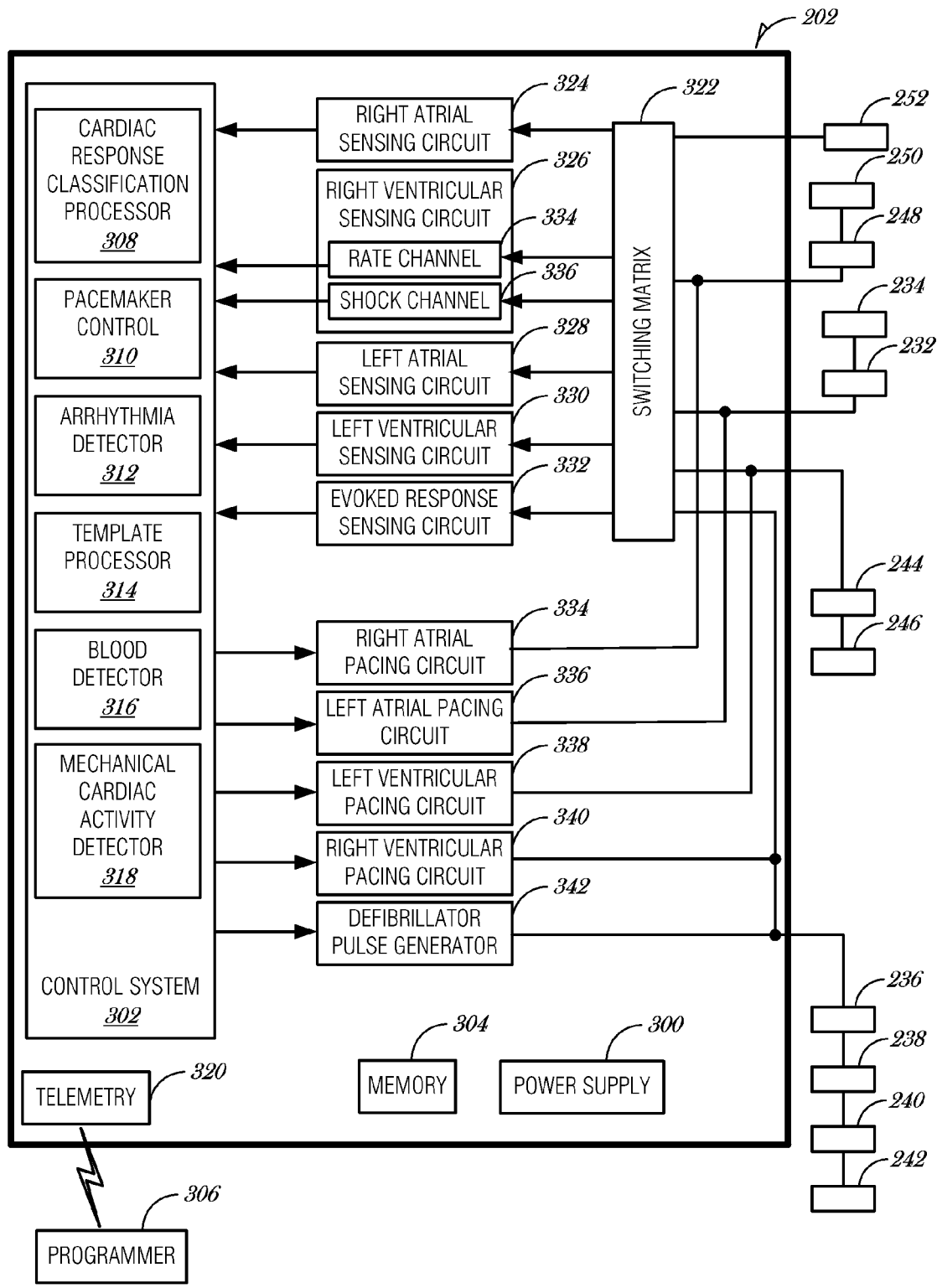
FIG. 3 is a block diagram illustrating an implantable medical device (IMD)

FIG. 3 is a block diagram illustrating an implantable medical device (IMD) 202. The IMD 202 can be suitable for therapy control based on electromechanical timing. The IMD 202 can be divided into functional blocks. It will be understood by those skilled in the art that there exist many possible configurations in which these functional blocks can be arranged and that the example illustrated in FIG. 3 is but one possible arrangement. In addition, although the IMD 202 contemplates the use of a programmable microprocessor-based logic circuit, other circuit implementations can be used.

The IMD 202 includes circuitry for receiving cardiac signals from a heart and delivering electrical stimulation energy to the heart in the form of pacing pulses and/or defibrillation shocks. In one embodiment, the circuitry of the PIMD 900 can be encased and hermetically sealed in a housing suitable for implanting in a human body. Power to the IMD 202 can be supplied by an electrochemical battery 300. A connector block (not shown) can be attached to the housing of the IMD 202 to provide for the physical and electrical attachment of the lead system conductors to the circuitry of the IMD 202.

The IMD 202 can be a programmable microprocessor-based system, including a control system 302 and a memory 304. The memory 304 can store parameters for various pacing, defibrillation, and sensing modes, along with other parameters. Further, the memory 304 can store data indicative of signals received by other components of the IMD 202. The memory 302 can be used, for example, for storing historical EMT/EMD information, blood oxygen levels, blood flow information, perfusion information, heart sounds, heart movement, EGM, and/or therapy data. The historical data storage can include, for example, data obtained from long-term patient monitoring used for trending or other diagnostic purposes. Historical data, as well as other information, can be transmitted to an external programmer 306 as needed or desired.

The control system 302 and memory 304 can cooperate with other components of the IMD 202 to control the operations of the IMD 202. The control system 302 incorporates a cardiac response classification processor 308 for classifying cardiac responses to pacing stimulation. The control system 302 can include additional functional components including a pacemaker control circuit 310, an arrhythmia detector 312, a template processor 314 for cardiac signal morphology analysis, and a blood detector 316 configured to determine blood perfusion, blood flow, and/or blood pressure based on one or more sensors. The control system 302 can optionally, or additionally, include a mechanical cardiac activity detector 318 configured to detect mechanical cardiac activity using sensor information from, for example, an accelerometer, a microphone, a pressure transducer, impedance sensors, or other motion or sound sensing arrangements.

A telemetry circuitry 320 can be implemented to provide communications between the IMD 202 and the external programmer 306. In an example, the telemetry circuitry 320 and the programmer 306 communicate using a wire loop antenna and a radio frequency telemetric link, to receive and transmit signals and data. In this manner, programming commands and other information can be transferred to the control system 302 from the programmer 306 during and after implant. In addition, stored cardiac data pertaining to EMT/EMD, capture threshold, capture detection and/or cardiac response classification, for example, along with other data, can be transferred to the programmer 306 from the IMD 202.

The telemetry circuitry 320 can also allow the IMD 202 to communicate with one or more receiving devices or systems situated external to the IMD 202. By way of example, the IMD 202 can communicate with a patient-worn, portable or bedside communication system via the telemetry circuitry 320. In one configuration, one or more physiologic or non-physiologic sensors (subcutaneous, cutaneous, or external of patient) can be equipped with a short-range wireless communication interface, such as an interface conforming to a known communications standard, such as Bluetooth or IEEE 802 standards. Data acquired by such sensors can be communicated to the IMD 202 via the telemetry circuitry 320. It is noted that physiologic or non-physiologic sensors equipped with wireless transmitters or transceivers can communicate with a receiving system external of the patient. The external sensors in communication with the IMD 202 can be used to determine electromechanical timing and/or delays in accordance with embodiments of the present invention.

As illustrated in FIG. 2 and reproduced in FIG. 3, one or more leads can be coupled to the IMD 202 to provide for sensing and therapy. In the example illustrated in FIG. 3, the electrodes include: RA-tip 248, RA-ring 250, RV-tip 240, RV-ring 242, RV-coil 238, SVC-coil 236, LV distal electrode 244, LV proximal electrode 246, LA distal electrode 234, LA proximal electrode 232, indifferent electrode 220, and can electrode 222 can be coupled through a switch matrix 322 to sensing circuits 324, 326, 328, 330, and 332.

A right atrial sensing circuit 324 serves to detect and amplify electrical signals from the right atrium of the heart. Bipolar sensing in the right atrium can be implemented, for example, by sensing voltages developed between the RA-tip 248 and the RA-ring 250. Unipolar sensing can be implemented, for example, by sensing voltages developed between the RA-tip 248 and the can electrode 222. Outputs from the right atrial sensing circuit 324 can be coupled to the control system 302.

A right ventricular sensing circuit 326 serves to detect and amplify electrical signals from the right ventricle of the heart. The right ventricular sensing circuit 326 can include, for example, a right ventricular rate channel 334 and a right ventricular shock channel 336. Right ventricular cardiac signals sensed through use of the RV-tip 240 electrode can be right ventricular near-field signals and can be denoted RV rate channel signals. A bipolar RV rate channel signal can be sensed as a voltage developed between the RV-tip 240 and the RV-ring 242. Alternatively, bipolar sensing in the right ventricle can be implemented using the RV-tip electrode 240 and the RV-coil 238. Unipolar rate channel sensing in the right ventricle can be implemented, for example, by sensing voltages developed between the RV-tip 240 and the can electrode 222.

Right ventricular cardiac signals sensed through use of the RV-coil electrode 238 can be far-field signals, also referred to as RV morphology or RV shock channel signals. More particularly, a right ventricular shock channel signal can be detected as a voltage developed between the RV-coil 238 and the SVC-coil 236. A right ventricular shock channel signal can also be detected as a voltage developed between the RV-coil 238 and the can electrode 222. In another configuration the can electrode 222 and the SVC-coil electrode 236 can be electrically shorted and a RV shock channel signal can be detected as the voltage developed between the RV-coil 238 and the can electrode 222/SVC-coil 236 combination.

Left atrial cardiac signals can be sensed through the use of one or more left atrial electrodes 232, 234, which can be configured as epicardial electrodes. A left atrial sensing circuit 328 serves to detect and amplify electrical signals from the left atrium of the heart. Bipolar sensing and/or pacing in the left atrium can be implemented, for example, using the LA distal electrode 234 and the LA proximal electrode 232. Unipolar sensing and/or pacing of the left atrium can be accomplished, for example, using the LA distal electrode 234 to can electrode 222 or the LA proximal electrode 232 to can electrode 222.

A left ventricular sensing circuit 330 serves to detect and amplify electrical signals from the left ventricle of the heart. Bipolar sensing in the left ventricle can be implemented, for example, by sensing voltages developed between the LV distal electrode 244 and the LV proximal electrode 246. Unipolar sensing can be implemented, for example, by sensing voltages developed between the LV distal electrode 244 or the LV proximal electrode 246 and the can electrode 222. Optionally, an LV coil electrode (not shown) can be inserted into the patient's cardiac vasculature, e.g., the coronary sinus, adjacent the left heart. Signals detected using combinations of the LV electrodes, 244, 246, LV coil electrode (not shown), and/or can electrode 222 can be sensed and amplified by the left ventricular sensing circuitry 330. The output of the left ventricular sensing circuit 330 can be coupled to the control system 302.

The evoked response sensing circuit 332 serves to sense and amplify voltages developed using various combinations of electrodes for cardiac response classification.

One or more of the sensing circuits 324, 326, 328, 330, 332 can include a sense amplifier (not shown), which receives intrinsic heart signals that include electrical depolarizations corresponding to heart contractions. The sense amplifier can detect such input heart depolarizations and provide an output electrical signal to the control system 302 or other portions of the IMD 202. In an example, the sense amplifier also includes filtering or other signal processing circuits for detecting the desired electrical depolarizations associated with heart contractions. The IMD 202 can also include an analog-to-digital (A/D) converter (not shown), which receives the sensed electrical depolarization signals and provides an output digital representation thereof. In an example, the A/D converter includes associated sample and hold circuits for sampling the electrical signal output by sense amplifier. A peak detector (not shown) can receive the digitized signal from A/D converter and detect signal peaks associated with heart contractions. These signal peaks can include R-waves in the QRS complexes associated with ventricular heart contractions. It is understood that the disclosed structure and techniques can also be used to detect atrial heart contractions using P-waves associated with atrial depolarizations.

The peak detector can output information about the timing of each R-wave to a heart interval extraction module (not shown). Based on this information, the heart rate interval extraction module provides a discrete-time signal that can be periodically sampled, e.g., the time difference between such samples can be uniform. Each such sample includes an associated time interval ("heart rate interval") corresponding to the detected heart rate.

The pacemaker control 310 located within the control system 302 communicates pacing signals to the RV-tip and RA-tip electrodes 240 and 248, respectively, according to a pre-established pacing regimen under appropriate conditions. Control signals, developed in accordance with a pacing regimen, can be initiated in the pacemaker control 310 transmitted to one or more pacing circuits: right atrial pacing circuit 334, left atrial pacing circuit 336, left ventricular pacing circuit 338, and right ventricular pacing circuit 340. In an example, pacing pulses may be provided to the right ventricle by the right ventricular pacing circuit 338, and/or to the right atrium by the right atrial pacing circuit 334.

Cardioversion or defibrillation control signals may be developed in the control system 302 to initiate a high energy pulse. High energy cardioversion or defibrillation pulses can be generated by the defibrillator pulse generator 342 in response to detection of fibrillation or tachycardia. The high energy cardioversion or defibrillation pulses can be directed through the leads to the right ventricle, for example, to terminate ventricular tachycardia or ventricular fibrillation.

Case Study

A study was conducted that analyzed various heart rate variability (HRV) measures during a controlled coronary artery occlusion of a test animal. Physiological data was collected pre and post-occlusion. The data included left ventricular pressures, heart sounds, and electrocardiogram (ECG) recordings. The left ventricular (LV) pressures were obtained using an invasive catheter, and the heart sounds were obtained using a surface accelerometer. From the ECG, R peaks were detected. These R peaks were used to identify RR intervals, which were then measured. The RR intervals were parsed into five-minute epochs and analyzed using twenty-three HRV metrics, which comprised a wide variety of time domain, frequency domain, time-frequency domain, and nonlinear metrics.

Specifically, the twenty-three variability metrics included eleven time domain metrics: mean, median, standard deviation of normal-to-normal beats (SDNN), inter-quartile range of normal-to-normal beats (IQRNN), coefficient of variation (CV), standard deviation of successive differences (SDSD), inter-quartile range of successive differences (IQRSD), normalized IQRSD (NIQRSD), root-mean-square of successive differences (RMSSD), coefficient of variation for successive differences (CVS) and percentage of differences between adjacent normal-to-normal intervals that are >50 msec (pNN50); four frequency domain metrics: power in the high- and low-frequency range (HF, LF), power ratio (LF/HF), and total power; three time-frequency metrics: high- and low-frequency wavelet power (HFW, LFW) and power ratio (LFW/HFW); and five nonlinear metrics: approximate entropy (ApEn), X-Y scatter from Poincaré plot (SigXY), fractal dimension (FD), and detrended fluctuation analysis (DFA1 and DFA2).

The R peaks were also used to cue hemodynamic measurements from LV pressures and heart sounds. The LV pressure signal was first parsed using the R wave markers to extract individual beats. Each beat was then differentiated to generate the LV dP/dT signal. Using a 200 ms window starting after the R peak location, the max value of the LV dP/dT (max dP/dT) was extracted. Max dP/dT can be used as the reference measure to quantify the reduction in LV performance (contractility) due to ischemia.

The R peaks were also used to parse the heart sounds signal. First each heart sound beat was obtained using the R peak marker. Each waveform was then filtered with a band-pass filter with cut-off frequencies between 20 Hz and 90 Hz. A 250 ms window after the R peak was used to measure the candidate S1 peaks. A dynamic programming-based tracking algorithm was then used to measure the largest, most consistent S1 peak for the duration of the study.

Figure 4:
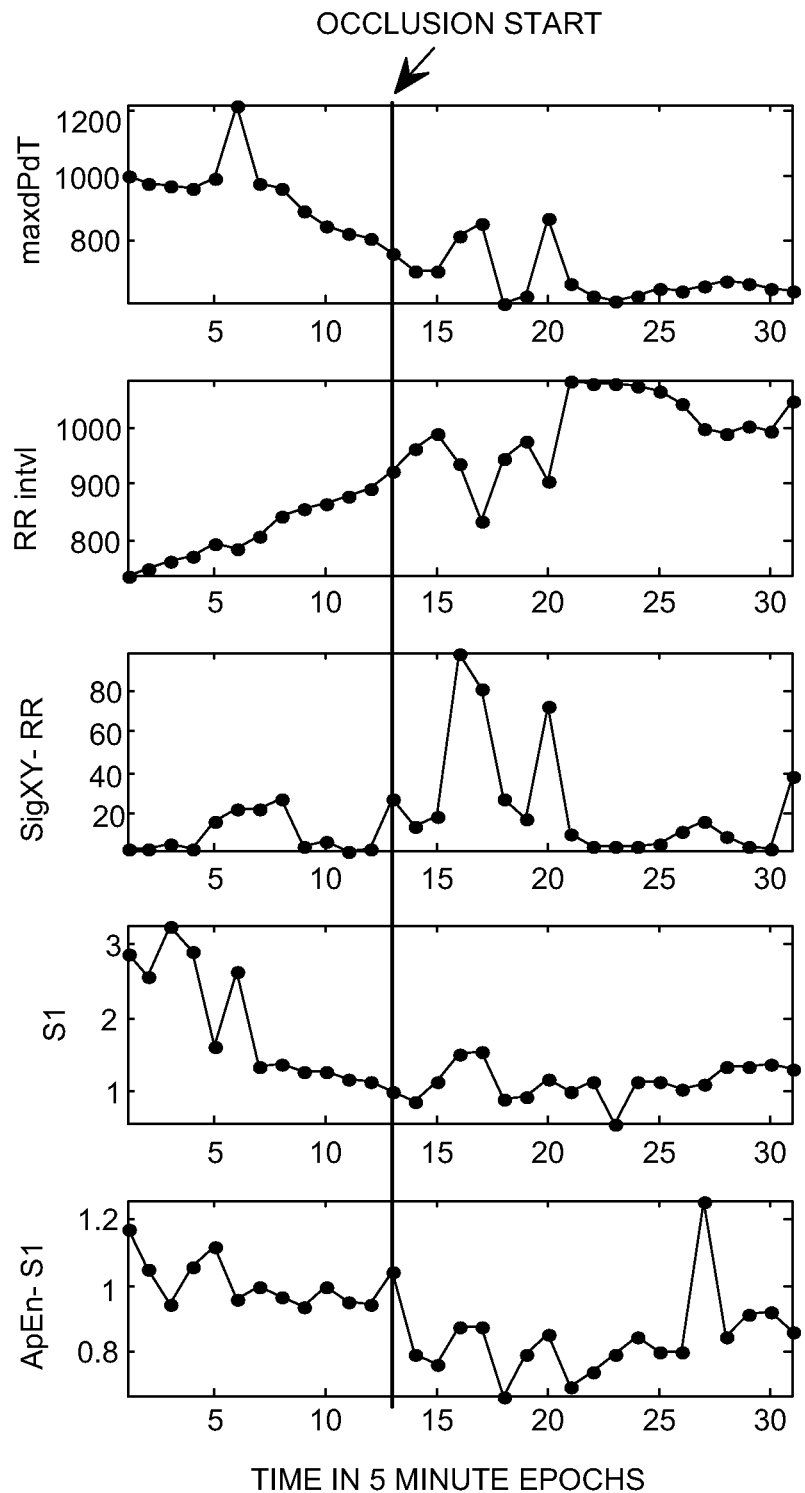
FIG. 4 is a group of graphs illustrating the max dP/dT, RR interval, and S1 amplitude along with the two non-linear variability metrics of RR interval and S1 amplitude.

A representative dataset can be presented to show an example of the relationships between the different parameters (e.g., RR interval, max dP/dT and S1 amplitude) and certain variability metrics. FIG. 4 is a group of graphs illustrating the max dP/dT, RR interval, and S1 amplitude along with the two non-linear variability metrics of RR interval and S1 amplitude. The variability metrics shown appear to be the most predictive of changes in LV performance (max dP/dT) due to ischemia. During the course of the study, the max dP/dT decreased; dropping significantly post occlusion. The balloon inflation occlusion resulted in a reflex increase in contractility, possibly due to the autonomic compensatory mechanisms. The increase in contractility was also reflected in changes in the RR interval and the SigXY derived from RR intervals. Periods immediately after the balloon inflation had relatively higher SigXY, possibly due to an autonomic reflex.

During the ischemia protocol the LV contractility, as measured by the max dP/dT, reduced on an average by 18.5%. No consistent relationship was found between the ischemic mass measured during necropsy and the change in max dP/dT. To evaluate changes due to ischemia the change in max dP/dT was used as the reference for the LV contractility change.

Figure 5:
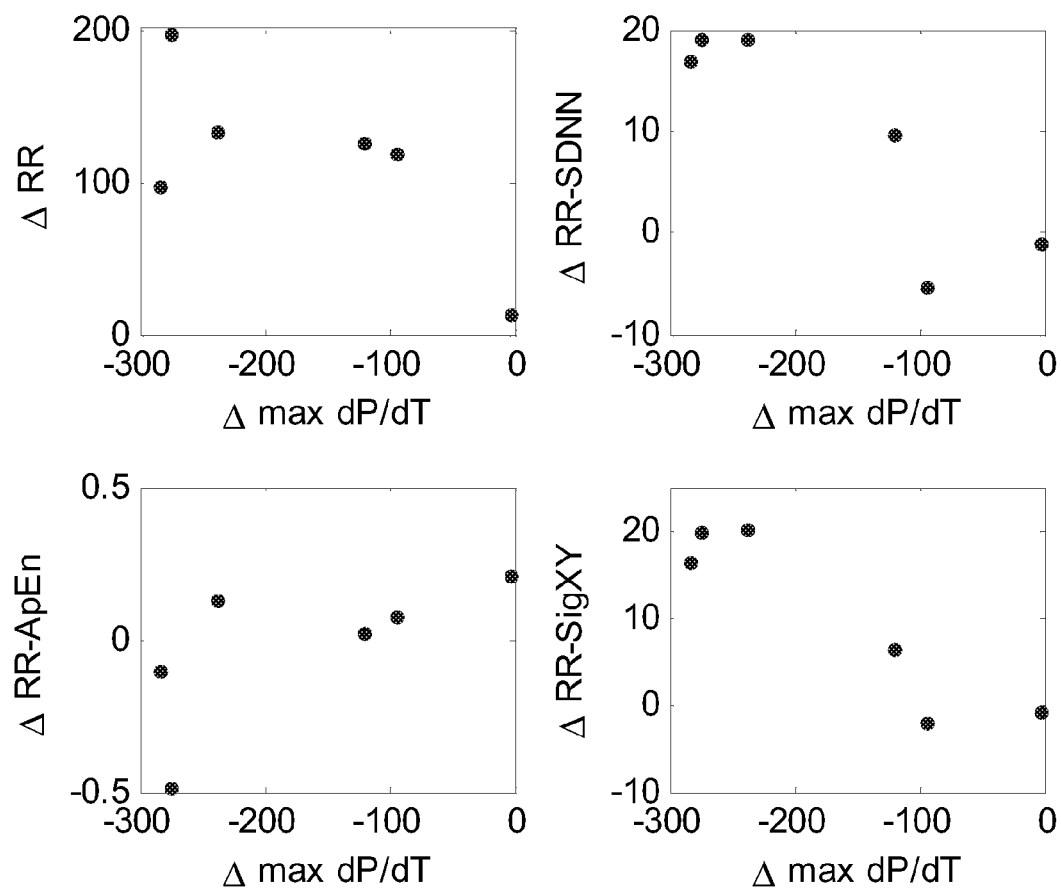
FIG. 5 is a group of scatterplots that illustrate an example of the relationships between changes in selected HRV metrics and changes in max dP/dT.

The twenty-three metrics referred to above were measured for the RR intervals from all five-minute epochs during the protocol. The metrics were analyzed before and after occlusion and the change in these metrics was compared to the change in max dP/dT. Many of the variability metrics were well correlated to the change in max dP/dT. FIG. 5 is a group of scatterplots that illustrate an example of the relationships between changes in selected HRV metrics and changes in max dP/dT. FIG. 6 is a table illustrating relationships between RR interval-based variability metrics, contractility variability metrics, and max dP/dT. While linear measures of RR intervals showed moderate correlation with max dP/dT (r~0.7), some of the nonlinear measures, such as the X-Y spread from a Poincaré plot (SigXY) of RR intervals, showed a higher correlation with max dP/dT (r=−0.92). Referring again to FIG. 5, the scatterplots highlight that while the RR intervals may not be highly correlated to changes in contractility during ischemia, the variability parameters (e.g., SigXY) can provide additional predictive information.

Figure 7:
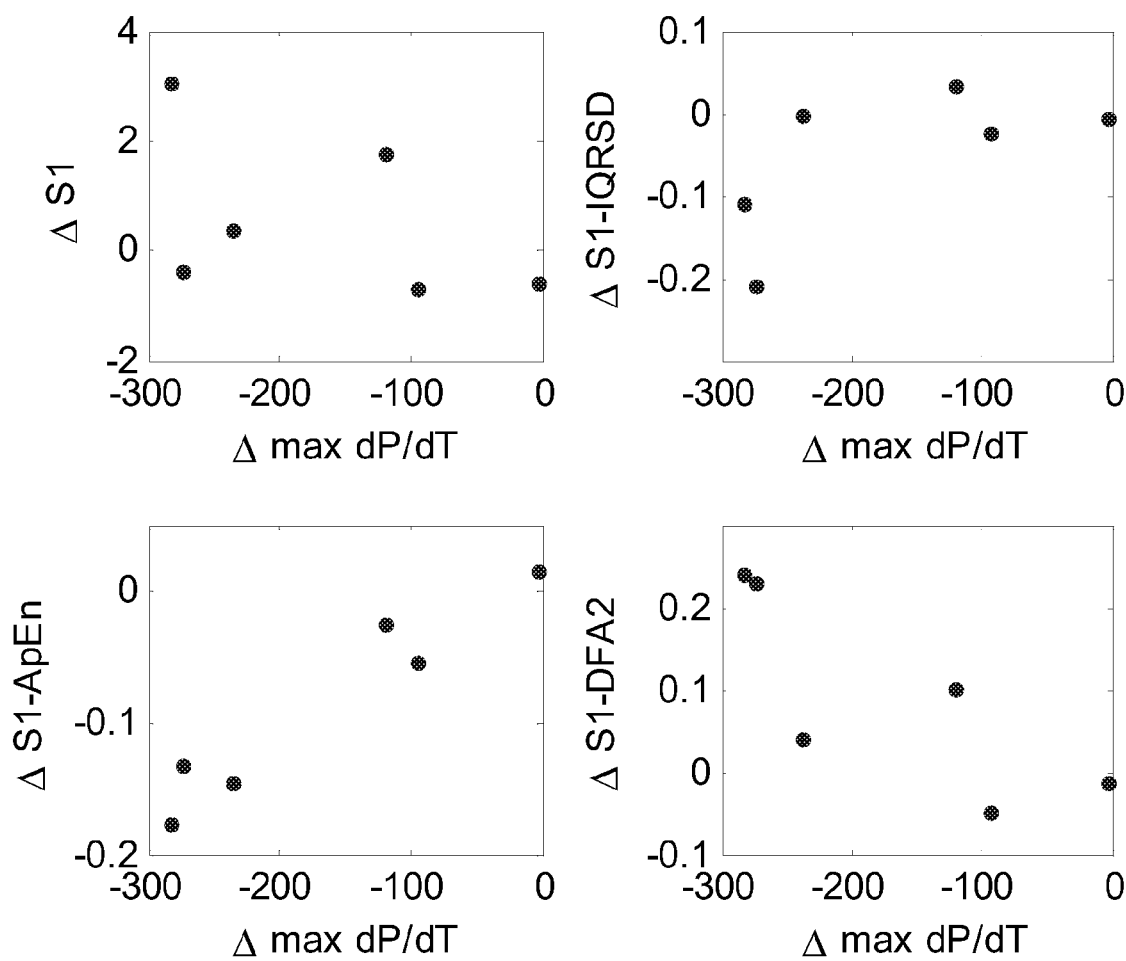
FIG. 7 is a group of scatterplots that illustrate an example of the relationships between changes in selected S1 variability metrics and changes in max dP/dT.

The twenty-three metrics referred to above were also measured for the S1 amplitude for all five-minute epochs during the protocol. The change in these metrics before and after occlusion was then compared to the change in max dP/dT during the corresponding periods. FIG. 7 is a group of scatterplots that illustrate an example of the relationships between changes in selected S1 variability metrics and changes in max dP/dT. Referring again to FIG. 6, examples of all the relationships between changes in S1 interval based variability metrics and max dP/dT is shown. It was observed that while there was a mild correlation between the change in S1 amplitude-based metrics and the change in max dP/dT, at least one of the nonlinear measures, e.g., the ApEn of the S1 amplitude, was highly correlated (r=0.96) with the change in contractility due to ischemia.

As discussed, multiple linear and non-linear variability metrics of RR interval and S1 amplitude can be used for ischemia detection. Changes in HRV (SigXY) and S1 (ApEn) can be highly correlated to changes in LV contractility, as measured by max dP/dT, during a balloon occlusion protocol. These findings may be related to changes in the autonomic tone during an ischemic event as a mechanism to compensate for the increased cardiac stress. The variability, as calculated by nonlinear measures, of signals from two noninvasive sensors, ECG and phonocardiogram, can be highly correlated to the changes of LV pressure.

Example Operations

Figure 8:
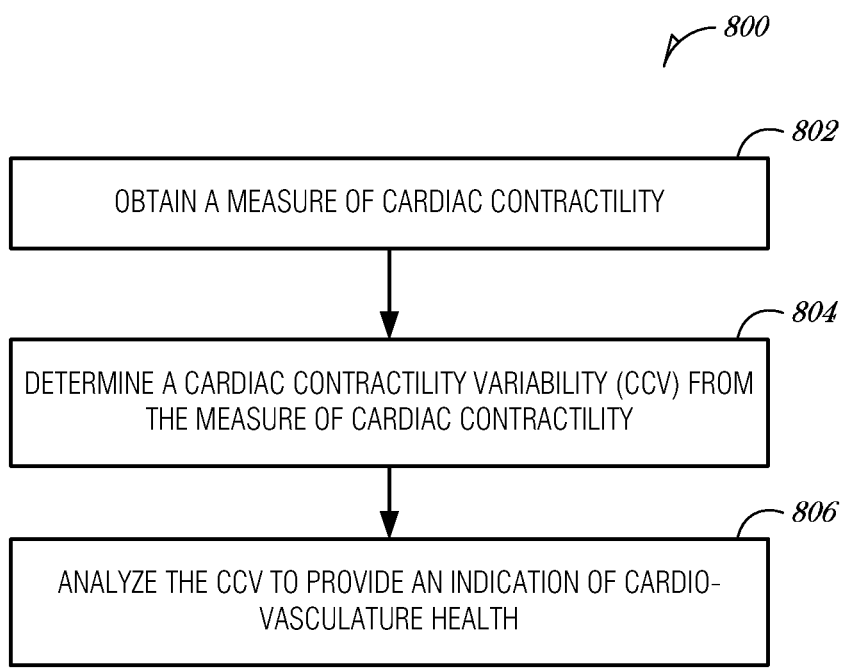
FIG. 8 is a flow chart illustrating a method for producing an indication of cardio-vasculature health.

FIG. 8 is a flow chart illustrating a method 800 for producing an indication of cardio-vasculature health. At 802, a measure of cardiac contractility can be obtained. Cardiac contractility can be obtained in various ways. In an example, the measure of cardiac contractility can be obtained by measuring at least one of a heart sound, a pulmonary artery pressure, a coronary venous pressure, a left ventricular pressure, a right ventricular pressure, or a timing interval.

At 804, a cardiac contractility variability (CCV) can be determined from the measure of cardiac contractility. Variability can be determined over various time intervals, such as a five-minute epoch, a twenty-minute epoch, or by larger intervals such as hourly, daily, weekly, monthly, and the like.

In an example, the CCV can be determined by using a time domain variability parameter to measure cardiac contractility variability. Time domain parameters can include mean, median, standard deviation of normal-to-normal beats (SDNN), inter-quartile range of normal-to-normal beats (IQRNN), coefficient of variation (CV), standard deviation of successive differences (SDSD), inter-quartile range of successive differences (IQRSD), normalized IQRSD (NIQRSD), root-mean-square of successive differences (RMSSD), coefficient of variation for successive differences (CVS) and percentage of differences between adjacent normal-to-normal intervals that are >50 msec (pNN50), along with other parameters that are a function of time.

In an example, the CCV can be determined by using a frequency domain variability parameter to measure cardiac contractility variability. Frequency domain parameters can include power in the high- and low-frequency range (HF, LF), power ratio (LF/HF), and total power, along with other parameters that are a function of frequency.

In an example, the CCV can be determined by using a time-frequency domain variability parameter to measure cardiac contractility variability. Time-frequency domain parameters can include high- and low-frequency wavelet power (HFW, LFW) and power ratio (LFW/HFW), along with other parameters that are a function of time and frequency.

In an example, the CCV can be determined by using a nonlinear variability parameter to measure cardiac contractility variability. Nonlinear variability parameters include approximate entropy (ApEn), X-Y scatter from Poincaré plot (SigXY), fractal dimension (FD), and detrended fluctuation analysis (DFA 1 and DFA2), along with other parameters that are not included in the time, frequency, and time-frequency parameters. In a further example, using the parameter from the class of nonlinear variability parameters includes measuring an approximate entropy (ApEn) of an S1 amplitude.

In an example, determining the cardiac contractility variability can be performed using a time period to provide a variability measurement. In an example, the time period can be an epoch having a duration of thirty seconds to twenty-four hours. In a specific example, the time period can be a five-minute epoch. In additional examples, other periodic intervals can be used, such as a daily, monthly, quarterly period, or the like.

Analyzing the cardiac contractility variability can include trending the variability measurement to provide a trended variability measurement. The trended variability measurement can then be compared to a threshold value to provide a comparison and using the comparison, a cardiac state can be detected. In an example, a baseline value can be used in the comparison. The baseline value can be used in place of or in addition to a threshold value. For example, the lesser of a baseline value and a threshold value can be used in the comparison. As another example, a mathematical function relating a baseline value and a threshold value can be used, such as the average of the two values. The baseline value can be established using an individual patient history, a patient population, a clinical study, general acknowledgement in a medical community of acceptable or target values, or the like.

At 806, the CCV can be analyzed to provide an indication of cardio-vasculature health. In an example, the indication of cardio-vasculature health can be related to an ischemic cardiac state. For example, a higher amount of variability can be associated with a healthier cardiac state. Conversely, a low CCV can be indicative of an ischemic cardiac state. Thresholds, filters, trending, and other methods can be used to detect a particular indication of cardio-vasculature health based on a particular CCV value.

In an example, trending of the CCV can be performed independent from analysis of the trended data. For example, CCV can be trended over one or more periods and then the trended data can be provided to a person, a system or a process. The trended CCV can then be used in various ways, such as by a clinician to evaluate the progression of a disease state, or by researchers to investigate correlations between cardiac contractility variability and other cardio-vasculature conditions.

In a further example, after determining the cardiac contractility variability, at least one of: a CRT timing parameter, a lead position, or an electrical position can be adjusted. The contractility variability can be measured again after the adjustment and can then be continually adjusted to increase the cardiac contractility variability. A decrease in CCV can be correlated with a general worsening of heart failure. However, in the case where a person is experiencing a higher-than-normal CCV, decreasing CCV can be used to adjust the person's CCV toward normal levels. Thus, although an example includes adjustments to increase CCV, it is understood that after determining the CCV, continual adjustments to one or more of a CRT timing parameter, a lead position, or an electrical position can be made to raise or lower CCV in order to achieve a normal or target CCV.

In addition, or in the alternative, other therapies can be adaptively adjusted based on one or more CCV measurements over time. For example, drug therapy, exercise therapy, or the like can be adjusted to improve CCV (either increase or decrease CCV to bring to a normal or target level).

In a further example, the cardiac contractility variability can be normalized by the measure of cardiac contractility. In a further example, the cardiac contractility variability can be normalized by an associated heart rate. By normalizing be either cardiac contractility of heart rate, or both, comparisons can be made easier and more accurate.

Figure 9:
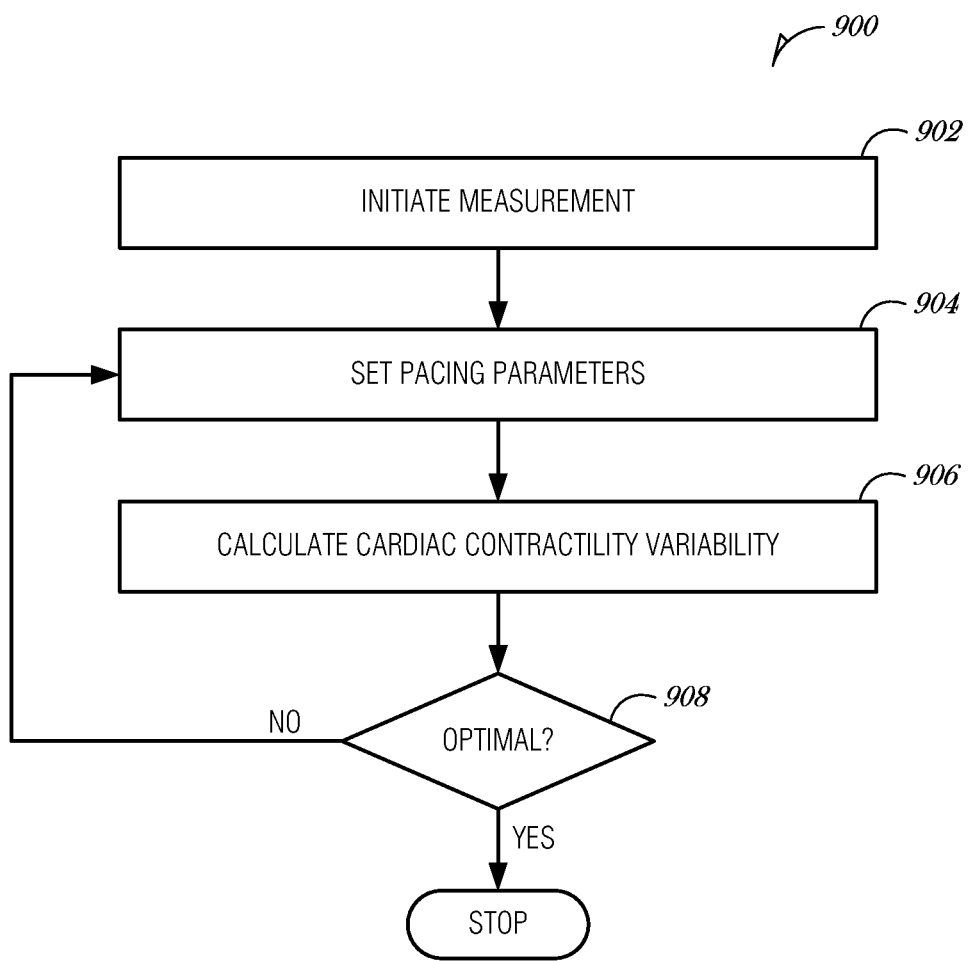
FIG. 9 is a flow chart illustrating a method for managing a patient device.

FIG. 9 is a flow chart illustrating a method 900 for managing a patient device. At 902, one or more measurements can be initiated. For example, heart sounds and an ECG can be obtained using internal or external devices. The ECG signal can be parsed to obtain R wave markers, which can then be used to extract individual beats in the heart sounds signal. Each beat can then be differentiated to generate an LV dP/dT signal. This provides a measurement of contractility from beat-to-beat. At 904, one or more pacing parameters can be set. Pacing parameters include, but are not limited to, parameters for various pacing, defibrillation, and sensing modes. For example, in the context of a pacing device, various parameters such as pacing amplitude, pacing rate, and pulse width can be configured or adjusted by a clinician or other care provider. At 906, cardiac contractility variability (CCV) can be determined. In an example, CCV can be determined by measuring approximate entropy of the S1 amplitude. In an example, CCV can be determined using the method 800, as described above. At 908, it can be determined whether the CCV is optimal or improving. If the CCV is not optimal, or at least improving, then the method 900 returns to block 904 to modify pacing parameters and the method 900 flows through to evaluate the CCV again at block 906. While pacing parameters are described with respect to FIG. 9, it is understood that any modification to a patient's device can be performed at block 904, such as lead repositioning or electrical repositioning, in an effort to optimize CCV. As an example, multiple sets of pacing parameters can be developed and used over time, tracking the effectiveness of each set as it is used and modifying pacing parameters to increase or optimize CCV.

Example Machine Architecture

Figure 10:
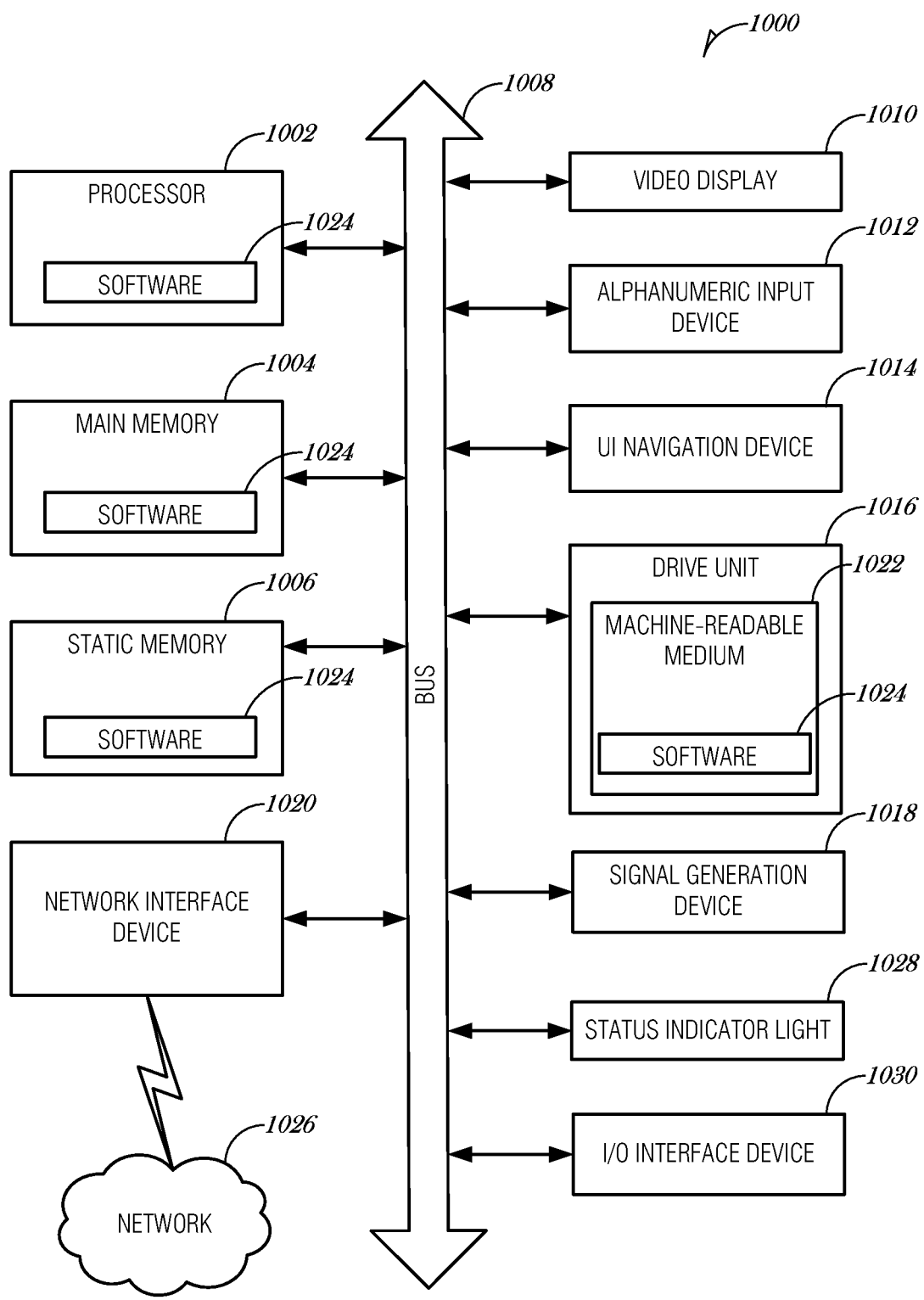
FIG. 10 is a block diagram illustrating a machine in the example form of a computer system, within which a set or sequence of instructions for causing the machine to perform any one of the methodologies discussed herein may be executed, according to various embodiments.

FIG. 10 is a block diagram of machine in the example form of a computer system 1000 within which a set of instructions, for causing the machine to perform any one or more of the methodologies discussed herein may be executed. In alternative examples, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a Personal Digital Assistant (PDA), a cellular telephone, a web appliance, a device programmer, a repeater, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor 1002 (e.g., a central processing unit (CPU) a graphics processing unit (GPU) or both), a main memory 1004 and a static memory 1006, which communicate with each other via a bus 1008. The computer system 1000 may further include a video display 1010 (e.g., a liquid crystal display (LCD) or a cathode ray tube (CRT)). The computer system 1000 also includes an alphanumeric input device 1012 (e.g., a keyboard), a user interface navigation device 1014 (e.g., a mouse), a disk drive unit 1016, a signal generation device 1018 (e.g., a speaker) and a network interface device 1020.

The disk drive unit 1016 includes a machine-readable medium 1022 on which is stored one or more sets of instructions (e.g., software 1024) embodying any one or more of the methodologies or functions described herein. The software 1024 may also reside, completely or at least partially, within the main memory 1004 and/or within the processor 1002 during execution thereof by the computer system 1000, the main memory 1004 and the processor 1002 also constituting machine-readable media. The software 1024 may further be transmitted or received over a network 1026 via the network interface device 1020.

While the computer system 1000 is shown with a processor 1002, it is understood that the systems and methods described herein can be implemented on one or more processors on one or more computer systems, including but not limited to a multi-processor computer (e.g., two or more separate processors or two or more cores in a single processor), a multi-computer system (e.g., a distributed computing environment), or a mixture of single-processor and multi-processor computers in a distributed fashion.

While the machine-readable medium 1022 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, tangible media, such as solid-state memories, optical, and magnetic media.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. The above description is intended to be illustrative, and not restrictive. For example, the above-described examples (or one or more aspects thereof) may be used in combination with each other. Other embodiments can be used, such as those identified by one of ordinary skill in the art upon review of the above description.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system, comprising:
   a non-transitory machine-readable medium; and
   one or more processors communicatively coupled to the machine-readable medium, the machine-readable media including instructions, which when executed by the one or more processors, cause the one or more processors to:
   obtain a measure of cardiac contractility;
   calculate a cardiac contractility variability from the measure of cardiac contractility, the cardiac contractility variability being a statistical measure of dispersion of the cardiac contractility;
   analyze the cardiac contractility variability to provide an indication of cardio-vascular health;
   after determining the cardiac contractility variability, adjust at least one of: a CRT timing parameter of an implantable medical device or an electrical position at which electrical therapy is delivered;
   measure the contractility variability after the adjusting; and
   continue to adjust in a closed-loop feedback manner to increase the cardiac contractility variability.

2. The system of claim 1, wherein the instructions to obtain the measure of cardiac contractility comprise instructions to:
   obtain a measure at least one of a heart sound, a pulmonary artery pressure, a coronary venous pressure, a left ventricular pressure, a right ventricular pressure, or a timing interval to provide the measure of cardiac contractility.

3. The system of claim I, wherein the instructions to determine the cardiac contractility variability comprise instructions to:
   use a time domain variability parameter to measure cardiac contractility variability.

4. The system of claim 1, wherein the instructions to determine the cardiac contractility variability comprise instructions to:
   use a frequency domain variability parameter to measure cardiac contractility variability.

5. The system of claim 1, wherein the instructions to determine the cardiac contractility variability comprise instructions to:
   use a time-frequency domain variability parameter to measure cardiac contractility variability.

6. The system of claim 1, wherein the instructions to determine the cardiac contractility variability comprise instructions to:
   use a nonlinear variability parameter to measure cardiac contractility variability.

7. The system of claim 6, wherein the instructions to use the parameter from the class of nonlinear variability parameters comprise instructions to:
   measure an approximate entropy (ApEn) of an S1 amplitude.

8. The system of claim 1, wherein the instructions to determine the cardiac contractility variability are performed using a time period to provide a variability measurement and wherein the instructions to analyze the cardiac contractility variability comprise instructions to:
trend the variability measurement to provide a trended variability measurement;
compare the trended variability measurement to a threshold value to provide a comparison; and
use the comparison to detect a cardiac state.

9. The system of claim 1, wherein the machine-readable medium includes instructions, which when executed by the one or more processors, cause the one or more processors to:
normalize the cardiac contractility variability by the measure of cardiac contractility.

10. The system of claim 1, wherein the machine-readable medium includes instructions, which when executed by the one or more processors, cause the one or more processors to:
normalize the cardiac contractility variability by an associated heart rate.

11. A method, comprising:
obtaining a measure of cardiac contractility using a sensor;
calculating by a processor-based device a cardiac contractility variability from the measure of cardiac contractility, the cardiac contractility variability being a statistical measure of dispersion of the cardiac contractility;
analyzing, at the processor-based device, the cardiac contractility variability to provide an indication of cardio-vascular health;
presenting, via the processor-based device, the indication of cardio-vascular health to a user:
after determining the cardiac contractility variability, adjusting at least one of: a CRT timing parameter of an implantable medical device, a lead position, or an electrical position at which electrical therapy is delivered;
measuring the contractility variability after the adjusting; and
continuing adjusting in a closed-loop feedback manner to increase the cardiac contractility variability.

12. The method of claim 11, wherein obtaining the measure of cardiac contractility comprises:
obtaining a measure at least one of a heart sound, a pulmonary artery pressure, a coronary venous pressure, a left ventricular pressure, a right ventricular pressure, or a timing interval to provide the measure of cardiac contractility.

13. The method of claim 11, wherein determining the cardiac contractility variability comprises:
using a time domain variability parameter to measure cardiac contractility variability.

14. The method of claim 11, wherein determining the cardiac contractility variability comprises:
using a frequency domain variability parameter to measure cardiac contractility variability.

15. The method of claim 11, wherein determining the cardiac contractility variability comprises:
using a time-frequency domain variability parameter to measure cardiac contractility variability.

16. The method of claim 11, wherein determining the cardiac contractility variability comprises:
using a nonlinear variability parameter to measure cardiac contractility variability.

17. The method of claim 11, wherein determining the cardiac contractility variability is performed using a time period to provide a variability measurement and wherein analyzing the cardiac contractility variability comprises:
trending the variability measurement to provide a trended variability measurement;
comparing the trended variability measurement to a threshold value to provide a comparison; and
using the comparison to detect a cardiac state.

18. A method comprising:
measuring cardiac contractility based on a plurality of cardiac cycles sensed by a sensor;
calculating, by a process-based device, cardiac contractility variability from the measured cardiac contractility, the cardiac contractility variability being a statistical measure of dispersion of the cardiac contractility;
identifying a target cardiac contractility variability value; and
adjusting at least one of: a CRT timing parameter of an implantable medical device, a lead position, or an electrical position at which electrical therapy is delivered, based on the cardiac contractility variability, to adjust the cardiac contractility variability toward the target cardiac contractility variability value.

* * * * *